United States Patent
Hirouchi et al.

(10) Patent No.: US 6,516,221 B1
(45) Date of Patent: Feb. 4, 2003

(54) BIO-CHARACTERISTIC VALUE MEASURING DEVICE WITH GRAPHICAL DISPLAY

(75) Inventors: Masaru Hirouchi, Tachikawa (JP); Masato Kodama, Tokyo (JP); Kazuhiko Sakata, Saitama (JP)

(73) Assignee: Tanita Corporation, Tokyo (JP)

( * ) Notice: Subject to any disclaimer, the term of this patent is extended or adjusted under 35 U.S.C. 154(b) by 20 days.

(21) Appl. No.: 09/697,166

(22) Filed: Oct. 27, 2000

(30) Foreign Application Priority Data

Oct. 27, 1999 (JP) .......................... 11-304770
Aug. 29, 2000 (JP) ....................... 2000-258632

(51) Int. Cl.⁷ ............................................. A61B 5/05
(52) U.S. Cl. ..................................................... 600/547
(58) Field of Search ................. 600/547; 382/168–180; 482/1, 2, 3, 4, 5, 6, 7, 8, 9

(56) References Cited

U.S. PATENT DOCUMENTS 6,308,096 B1 * 10/2001 Masuo ....................... 600/547
6,354,996 B1 * 3/2002 Drinan et al. ............... 600/300

FOREIGN PATENT DOCUMENTS

JP          8-150130         6/1996

* cited by examiner

Primary Examiner—Max F. Hindenburg
Assistant Examiner—Pamela Wimgood
(74) Attorney, Agent, or Firm—McDermott, Will & Emery

(57) ABSTRACT

An object of the present invention is to provide a user with a bio-characteristic index in an easily realizable manner by controlling and displaying said index in a long-term viewpoint, and, in particular, to display a transition of user's body fat in an easily sensible manner and to provide a body fat meter employing such display system which allows the user to execute a preferable dieting and to exercise a management of his (her) body weight and body fat.

The body fat meter of the present invention graphically displays on a display section simultaneously a daily, a weekly and a monthly variations of past body fat mass stored in a storage section. Further, variation of body weight values is displayed together with that of the body fat mass simultaneously in the same manner thereto. This allows the user to detect an unreasonable dieting where only the fat free tissue decreases but the body fat doesn't decrease, and provides the user with a safe and healthy weight and body fat management system.

11 Claims, 5 Drawing Sheets

BIO-CHARACTERISTIC VALUE MEASURING DEVICE WITH GRAPHICAL DISPLAY

BACKGROUND OF THE INVENTION

1. Field of the Invention

The present invention relates to a display method of a measuring device for measuring bio-characteristic indexes such as weight or body fat mass.

2. Description of the Prior Art

Recently, there appears in a field of health care a trend to lay stress on a body fat rate rather than a weight. In particular, a person with high body fat rate is, even if a weight thereof is less than a standard weight value, called to be of "latent obesity" and is considered to be problematic from a health viewpoint. A type of distribution of body fat depends on the individual, and having fat accumulated in an internal organ is thought to be problematic. This visceral fat type obesity means a condition where fat is accumulated in tissues of a mesentery in an abdomen, and is considered to have higher morbidity rate of various complications comparing with a subcutaneous fat type obesity. A person of visceral fat type obesity does not necessarily appear to be fat and has BMI (Body mass index) within a normal range, but has lots of visceral fat. In this case, he (she) is not categorized to be of obesity since he (she) does not have a fat physique, but he (she) is not in good condition from a health viewpoint.

A dieting is extensively carried on and is booming to reduce the body fat together with the body weight, but an unnatural dieting temporarily decreases a part of muscle and bone together with the fat. In addition, what is increased in a rebound (a phenomenon increasing weight again) is the fat which is easy to be accumulated in a body. That is, important elements such as muscle and bone or a fat free tissue remain in a weak condition and only the fat is accumulated. Thus, even if the weight after the rebound is the same with that before dieting, the body fat rate may be higher or sometimes it reaches up to the "latent obesity" condition. Repeat of the rebound phenomenon is called weight cycling, and because basal metabolism rate lowers as skeletal muscle decreases, physical constitution changes so as to get fat easily and to get lean hardly.

Under this situation, there is proposed a body fat meter which takes advantage of the scientific principle that the body fat can be evaluated by measuring a bioelectric impedance, and devices including the body fat meter incorporated therein are widely spreading into homes because of its easy handling. These kinds of devices cause an electric current between ends of a body of a person to be measured and measure a voltage applied therebetween to determine an impedance value of the body. Then the body fat rate at that time is calculated and displayed based on the determined impedance value and personal data including height, body weight, sex, age or the like of the person to be measured. Some of them are configured to store past data of the body fat rate, to display these values or to numerically display an increased/reduced body fat mass comparing with the past one.

It is not recommended to reduce body fat excessively in a short time from a viewpoint of burden to the body, but it is recommended to reduce it gradually during a long period. Since what is likely to be reduced by the excessive and short time dieting is the skeletal muscle, a body fat meter is required to easily judge whether body fat is reduced or not by such dieting.

The conventional body fat meter provides the data of the body fat rate or the body fat mass only at that time or allows comparison with past data or to see the change thereof by calling out their numerical data, but does not allow a long term transition or change thereof to be shown at a time. Further, since body fat rate decreases when weight increases by taking meals or water without increasing body fat, thereby decreasing the ratio of body fat to weight, it is problematic to exercise body fat management based only body fat rate.

Since physical conditions including body fat, weight, total body water volume and fat free mass are likely to vary depending on daily living conditions, it preferable to judge health based not only on daily variation but also on long-term variation.

The present invention is made in the light of the problems described above, and the object thereof is to make the transition of bio-characteristic indexes be easily realized by displaying long-term variation together with short-term variation thereof. Especially in the body fat meter, the object is to display in an easily sensible manner the long-term transition of body fat rate of the person to be measured, and to provide a device which allows the subject person to diet appropriately and to exercise management of weight and body fat using the inventive body fat meter.

SUMMARY OF THE INVENTION

A bio-characteristic value measuring device with graphical display comprises a measuring device, a storage device, and a display device, whereby said measuring device measures a bio-characteristic value, said storage device stores a measured characteristic value, and said display device graphically displays variations of characteristic values in at least first and second units of time simultaneously, said characteristic values in said first unit of time being defined by stored characteristic values, and said characteristic values in said second unit of time being defined by average values of characteristic values calculated based on a plurality of characteristic values in said first unit of time.

Further, a bio-characteristic value measuring device with graphical display comprises a measuring device, an input device, an arithmetic device, a storage device, and a display device, whereby said measuring device measures a bio-characteristic value, said input device inputs personal body information of a person to be measured, said arithmetic device evaluates a bio-characteristic index of said person to be measured based on the measured bio-characteristic value and an input personal body information thereof, said storage device stores an evaluated bio-characteristic index and said input personal body information, and said display device graphically displays variations of characteristic values in at least a first and a second units of time simultaneously, said characteristic value in said first unit of time being defined by stored past bio-characteristic indexes, and said characteristic values in said second unit of time being defined by average values of characteristic values calculated based on a plurality of index values in said first unit of time.

Further, a body weight scale of the present invention comprises a body weight measuring device, a storage device, and a display device, whereby said body weight measuring device measures a body weight, said storage device stores a measured body weight, and said display device simultaneously displaying a plurality of variations among a daily variation, a weekly variation and a monthly variation of stored past body weight values.

Further, a body fat meter of the present invention comprises an impedance measuring device, an input device, an arithmetic device, a storage device, and a display device, whereby said impedance measuring device measures a bio-electric impedance value, said input device inputs a personal body information of a person to be measured, said arithmetic device evaluates a body fat of said person to be measured based on a measured bioelectric impedance value and an input personal body information, said storage device stores an evaluated body fat and said input personal body information, and said display device graphically displays simultaneously a plurality of variations out of a daily, a weekly and a monthly variations of stored past body fat data.

Further, a body fat meter of the present invention comprises an impedance measuring device, a weight measuring device, an input device, an arithmetic device, a storage device, and a display device, whereby said impedance measuring device measures a bioelectric impedance value, said weight measuring device measures a body weight value, said input device inputs a personal body information of a person to be measured, said arithmetic device evaluates a body fat of said person to be measured based on a measured bioelectric impedance value and body weight value and an input personal body information, a storage device for storing an evaluated body fat data and said input personal body information, and said display device graphically displays simultaneously a plurality of variations out of a daily, a weekly and a monthly variations of stored past body fat data.

Further, in the body fat meter of the present invention, said display device graphically displays simultaneously all of the daily, the weekly and the monthly variations.

Further, in the body fat meter of the present invention, said display device graphically displays said variation during seven days with respect to said daily variation, the variation during twelve weeks with respect to said weekly variation and the variation during twelve months with respect to said monthly variation.

Further, in the body fat meter of the present invention, said display device is made of dot matrix type LCD, a bar graph is employed as a graph displayed on said dot matrix type LCD, and when a plurality of variations among said daily, said weekly and said monthly variations is displayed simultaneously, a variation in one period is indicated by all dots included in said bar graph showing values of said variations and another variation in another period adjacent to said one period is indicated only by dots for indicating said values of the variations.

Further, in the body fat meter of the present invention, said body fat displayed on said display device is a body fat mass which means a weight thereof.

DESCRIPTION OF THE PREFERRED EMBODIMENTS

A display section of a bio-characteristic value measuring device according to the present invention has a display portion which displays a variation of past bio-characteristic values or indexes during a certain period stored in a storing section and another display portion which displays average values in a second period composed of a plurality of said certain periods. That is, a short-term variation and a long-term variation are displayed simultaneously by additionally displaying the average value calculated based on the values of a plurality of short periods.

For example, the body fat meter of the present invention graphically displays on the display section a daily, a weekly and a monthly variations of the past body fat mass data stored in the storing section. Further, a variation of body weight values is also graphically displayed together with that of the body fat mass simultaneously.

As an embodiment of the bio-characteristic value measuring device of the present invention, a body fat meter for measuring a body weight and a bio-electric impedance as bio-characteristic values will be described with reference to the attached drawings.

Figure 1:
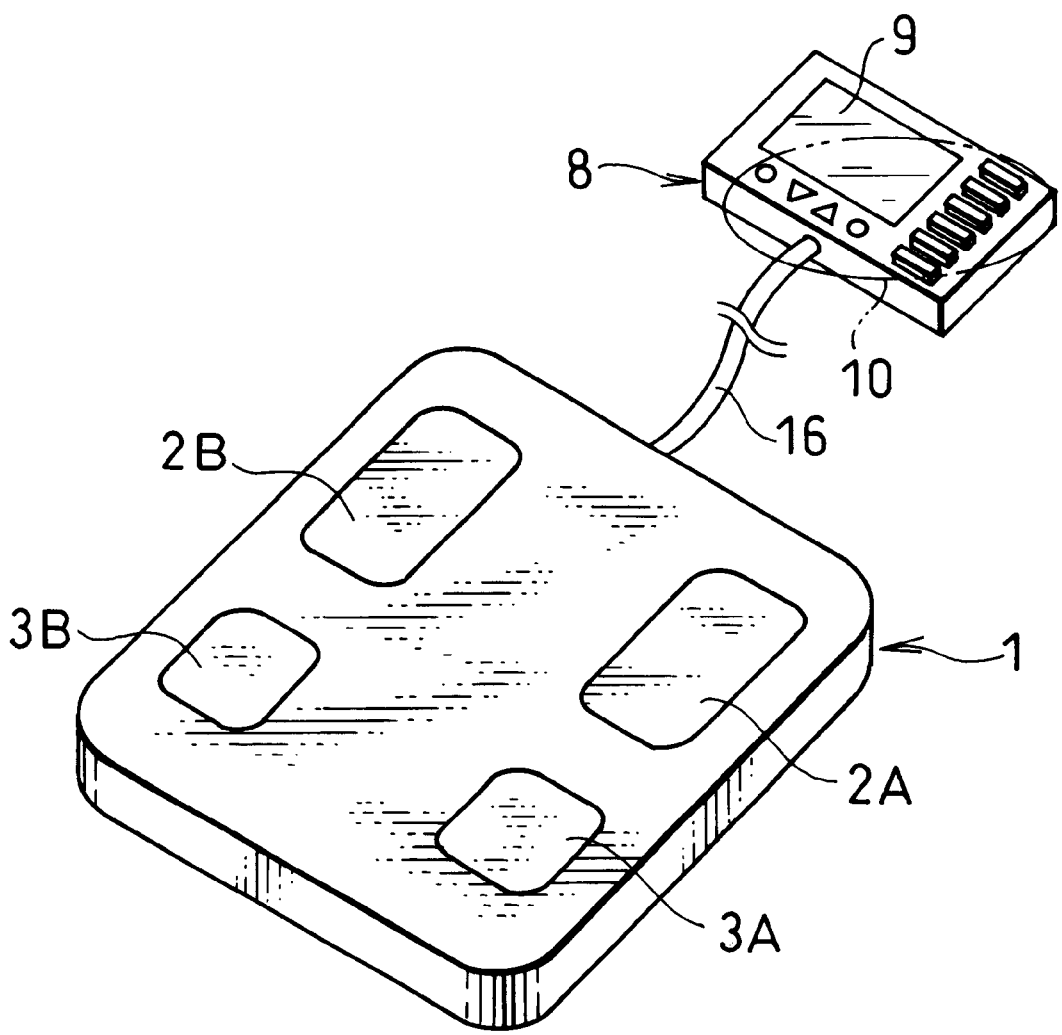
FIG. 1 is a perspective view of a body fat meter of an embodiment according to the present invention.
Figure 2:
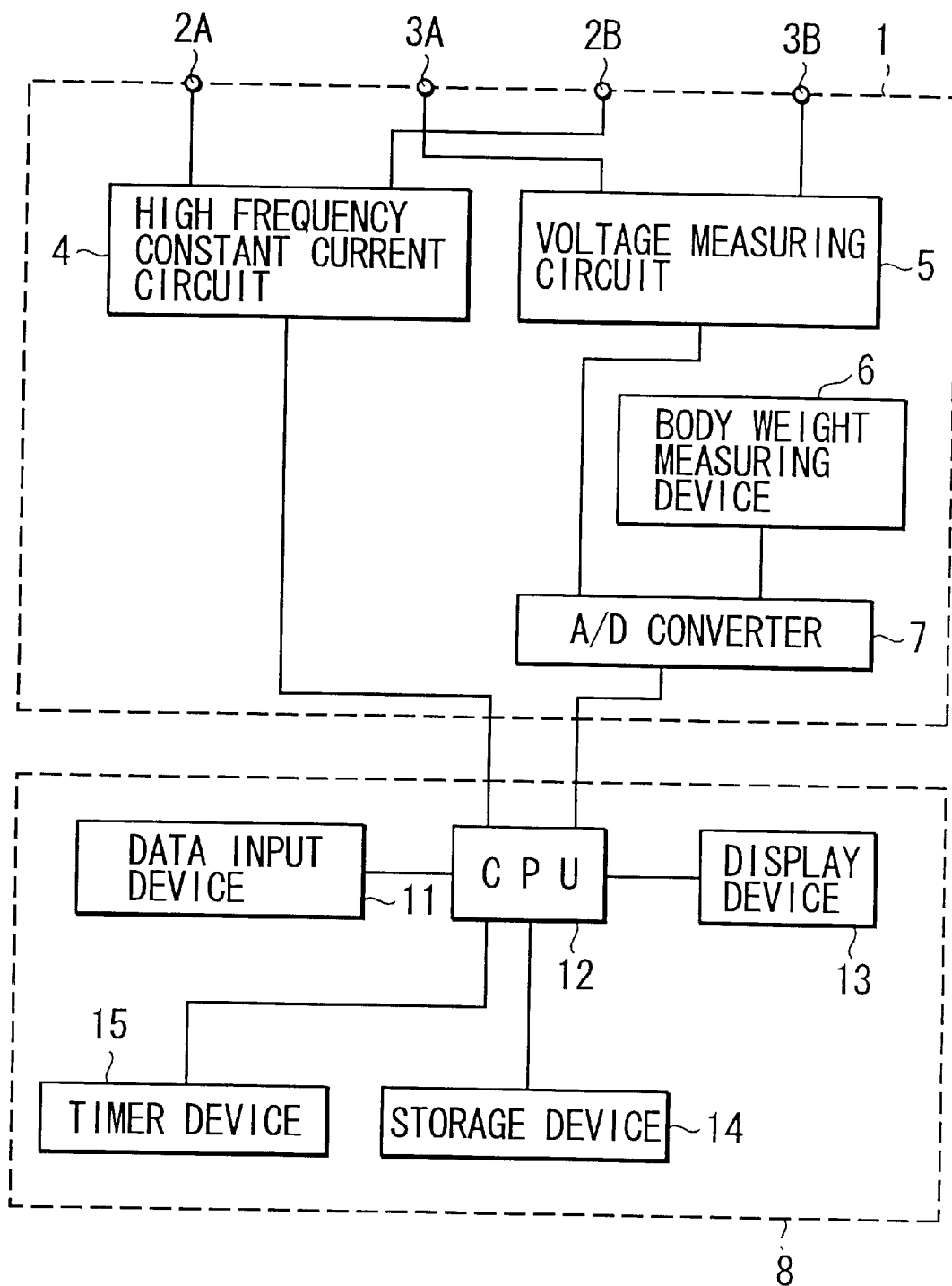
FIG. 2 is an electrical block diagram of the body fat meter of an embodiment according to the present invention.

FIG. 1 is a perspective view illustrating an external appearance of the body fat meter of an embodiment of the present invention. FIG. 2 is a block diagram illustrating an electrical arrangement of the body fat meter shown in FIG. 1.

Electrodes 2A, 2B, 3A and 3B are provided on a top surface of a body fat meter main body 1 and, as an impedance measuring device, a pair of electrodes 2A and 2B is connected to a high frequency constant current circuit 4 for applying a weak high frequency constant current therethrough so that an impedance between both feet may be measured. Another pair of electrodes 3A and 3B is connected to a voltage measuring circuit 5 for measuring a voltage drop by the above constant current. A weight measuring device 6 is installed within the body fat meter main body 1 as a weight measuring device which measures a body weight or a weight of person to be measured when he (she) put himself (herself) on the body fat meter main body 1. The voltage measuring circuit 5 and the weight measuring device 6 are connected to an A/D converter 7 for converting an analogue value to a digital value.

A control box 3 is provided with a display section 9 and a group of switches 10 to input various data. The control box 8 includes a data input device 11 comprising the group of switches 10 to set a personal body information of the person to be measured or to start the measurement, a CPU 12 comprising an arithmetic section which evaluates a body fat of the person to be measured based on the input personal body information and measured impedance and body weight values and a control section to control a result from the arithmetic section so as to be displayed and stored, a display device 13 which displays various data based on the above result, a storage device 14 which stores the measured data and the personal body information, and a timer device 15 used to manage a measurement date.

The control box 8 is connected electrically through a code 16 to the body fat meter main body 1, and the data of the impedance value and the body weight value measured by the body fat meter main body 1 are transmitted to the control box 8. Since being connected to the body fat meter main body 1 by the code 16 separated therefrom, the control box 8 can be placed in any position convenient of visibility to the person to be measured.

The CPU 12 arithmetically calculates the body fat rate and/or the body fat mass based on the received data and the set personal body information, and controls to graphically display on the display section 9 a transition of these data using the determined data and a past data stored in the storage device 14.

Figure 3:
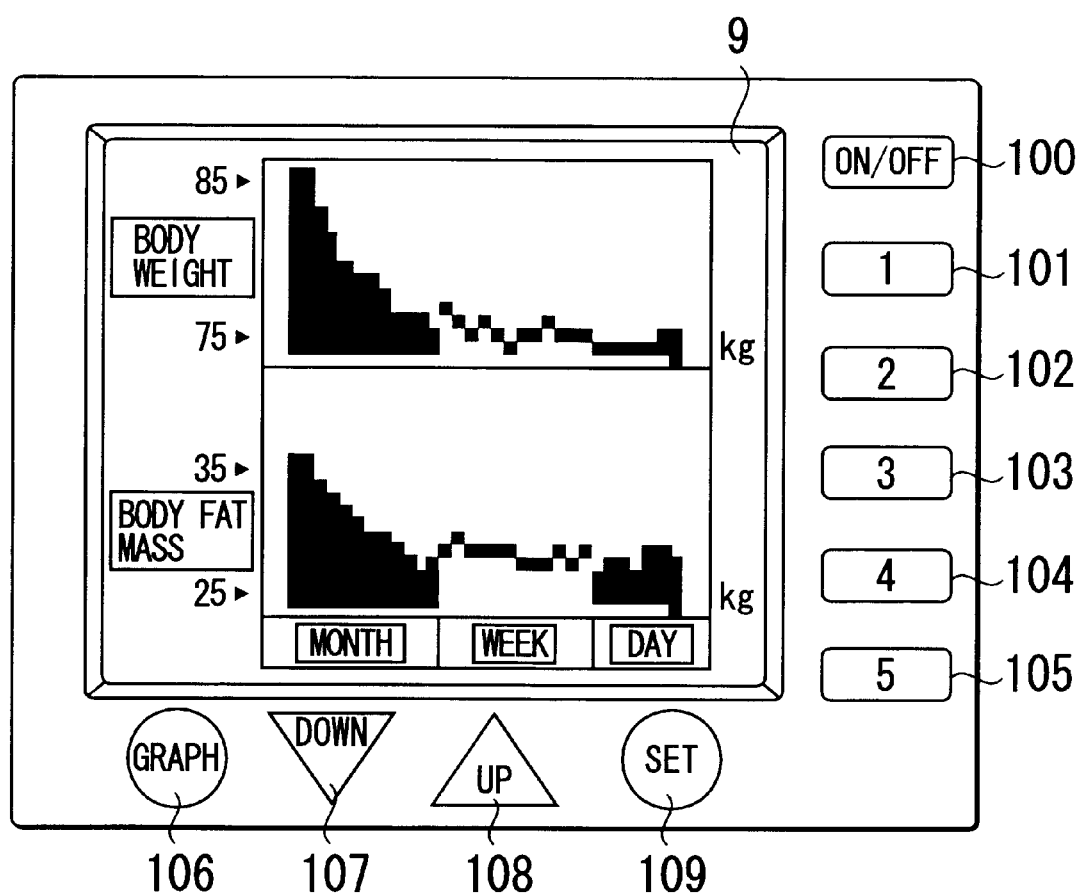
FIG. 3 is a schematic view of a control box of an embodiment according to the present invention.

FIG. 3 is an enlarged view of a main part of the control box 8. The display section 9 employs dot matrix type LCD capable of displaying a fine graphical illustration as well as characters. The body weight value and the body fat mass are graphically displayed in time sequence on an upper column and a lower column respectively and an x-axis is divided into a month, a week and a day sections. In this embodiment, one day is taken as a first unit of time, one week is taken as a second unit of time composed of plurality of averaged first units, and one month is taken as a third unit of time composed of plurality of averaged second units. As for the lengths of months, weeks and days, twelve months, twelve weeks and seven days can be displayed simultaneously, in which, as to the month section, twelve average values each being determined by an average during every one month starting from a previous month to the past are displayed, and as to the week section, twelve average values each being determined by an average during every one week starting from a previous week to the past are displayed, and also as to the day section, seven measured values each being measured during seven days starting from a current day to the past are displayed. Since this display system allows the variation during a period convenient for marking off a life cycle such as one week, three months and one year to be displayed simultaneously, a user can easily evaluate the transition of his (her) body fat and body weight in comparison with his (her) living condition. A y-axis indicates the body weight value in a body weight display area, and the body fat mass in a body fat mass display area respectively, and a scale width for one dot on the y-axis are configured to be properly adjusted so that past measured values may be displayed within the display section 9. Accordingly, scale values shown in a left side are changed to meet the values to be displayed.

The group of switches 10 includes a power switch 100, personal switches 101 to 105 for five persons, a graph switch 106, a down-switch 107, an up-switch 108 and a set switch 109.

Figure 4:
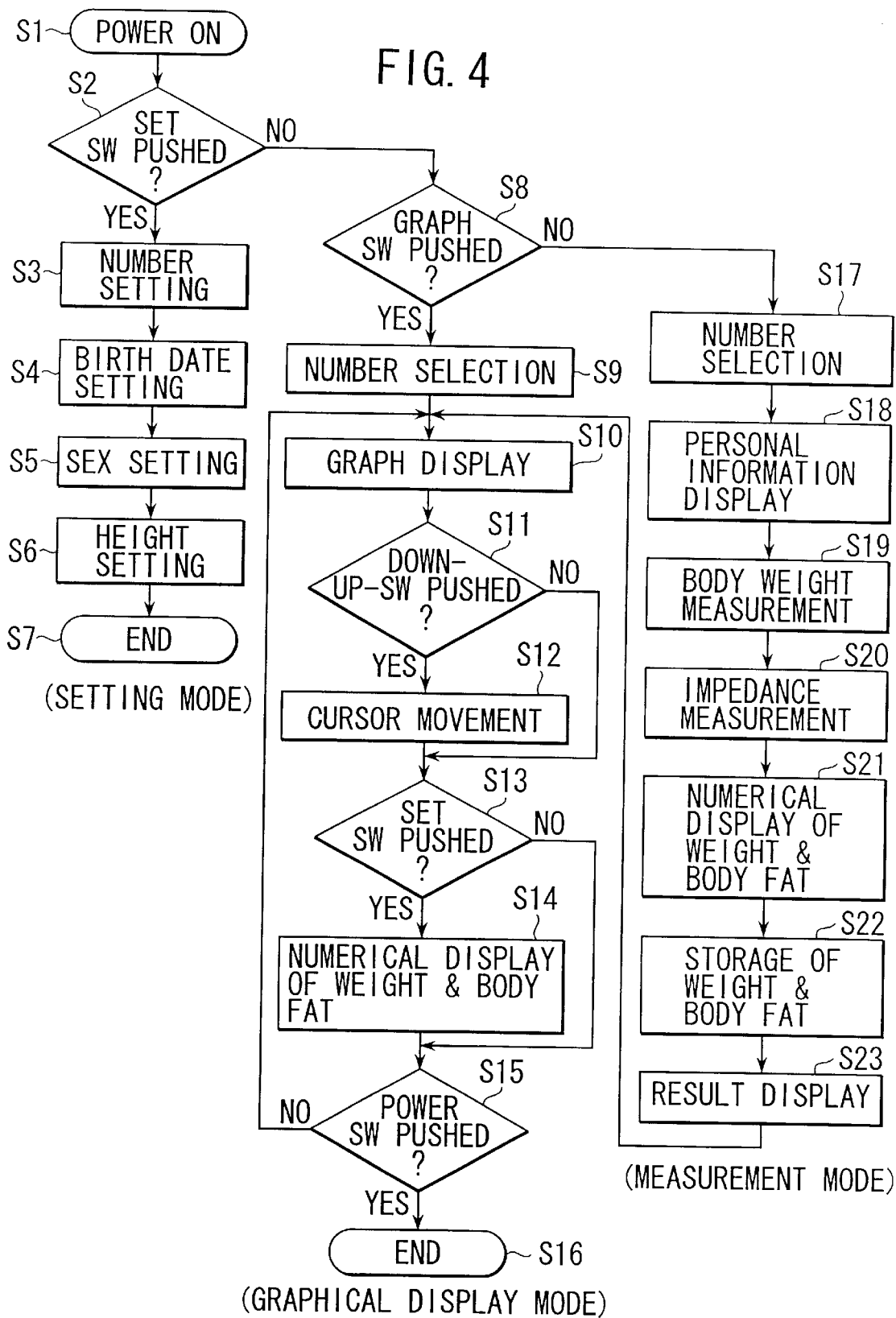
FIG. 4 is a flow chart illustrating an operation procedure of the body fat meter of an embodiment according to the present invention.

Then, a flow of setting a personal body information, measuring and graphically displaying in the body fat meter of the present embodiment will be described with reference to the flow chart of FIG. 4.

When the person to be measured pushes the power switch 100 on the control box 8, a power source of the body fat meter 1 is turned on (step S1). Then, whether the set switch 109 has been pushed or not is judged and if the set switch has been pushed here, the process moves to a setting mode (step S2).

In the setting mode, the personal body information of the person to be measured is input.

At first, one personal switch is selected out of the personal switches 101 to 105 as a memory number used to store the data and is pushed. Then the set switch 109 is pushed (step S3).

When the memory number has been set, then the date of birth of the person to be measured is input.

Since the current date is indicated in the display section as an initial value, down-switch 107 and the up-switch 108 are used to adjust the date. After the proper date is indicated, the set switch 109 is pushed (step S4). The date set here is used to determine an age of the person to be measured based on the current date stored in the timer device 15 to select a proper regression formula for determining the body fat mass, which depends on the age.

When the birth date has been set, then the sex data of the person to be measured is input.

Since "MAN" is indicated in the display section as an initial value, the down-switch 107 and the up-switch 108 are used to change it if necessary. Then the set switch 109 is pushed (step S5). The sex data set here is also used to select the proper regression formula for determining the body fat mass.

When the sex data has been set, then the height data of the person to be measured is input.

Since "170 cm" is indicated in the display section as an initial value, the down-switch 107 and the up-switch 108 are used to adjust it if necessary. Then, the set switch 109 is pushed (step S6). The height data set here is used as a parameter when the body fat mass is to be determined.

When the height data is input, setting of the personal body data of the person to be measured has been completed. All the data input here are stored in the storage device 14 (step S7).

In case where the set switch 109 has not been pushed in step S2, whether the graph switch 106 has been pushed or not is judged. When the graph switch 106 has been pushed, the process moves to a graphical display mode (step S8).

In the graphical display mode, the body weight value and the body fat mass are graphically displayed based on the past measured values.

One switch is selected out of the personal switches 101 to 105 as the memory number used for storing and is pushed. Then, the set switch 109 is pushed (step 9).

Figure 5:
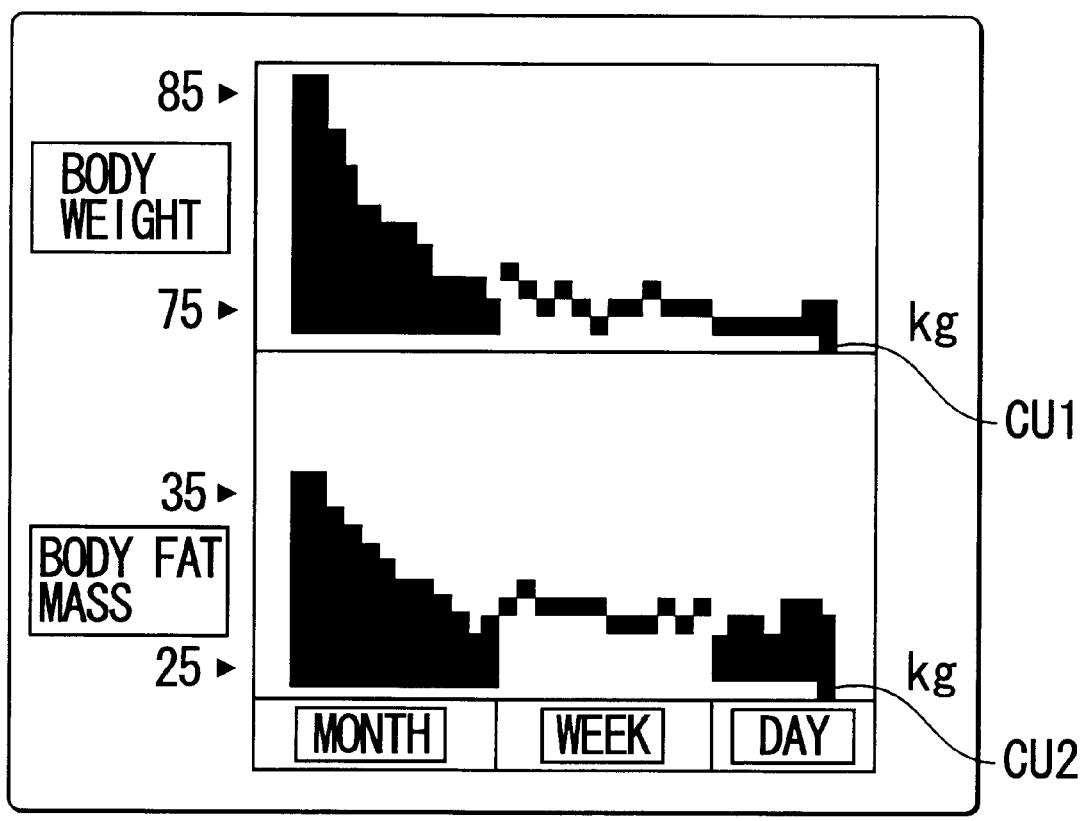
FIG. 5 shows contents of display of the body fat meter of an embodiment according to the present invention.

When the memory number has been selected, the past body weight and body fat mass values stored in the storage device 14 are called out therefrom and are graphically displayed on the display section 9 as shown in FIG. 5 (step S10). In FIG. 5, the data in the most right side of the day section indicates that of the current day and as it goes to the left side, the data therein becomes older. The same relation is applied to the week and the month sections, and accordingly, this example shows that both of the body weight and the body fat mass have been gradually reduced within this one year. In the graph of the week section, only the dots indicating the data in respective weeks are indicated and the dots below those are not indicated. This makes it easy to distinguish a border between the day section and the week section and also that between the week section and the year section.

Then, whether the down-switch 107 or the up-switch 108 has been pushed or not is judged (step S11). In FIG. 5, CU1 and CU2 indicate cursors, and when either switch is pushed here, the cursors CU1 and CU2 move toward a selected direction (step S12). The cursors CU1 and CU2 laterally move simultaneously with a pitch of one period (dot).

Then, whether the set switch 109 has been pushed or not is judged (step S13). When the set switch 109 has been pushed, the body weight and the body fat mass in the period or date indicated by the cursors CU1 and CU2 are shown by numerical values on the display section 9. When the period or date indicated thereby is the date, the measured values of the body weight and the body fat mass at that day are shown, and when it is the week, the average values of the body weight and the body fat mass during that week are shown, and when it is the month, the average values of the body weight and the body fat mass during that month are shown (step S14). When no measurement was made in the selected period or date and thereby no data has been stored, "NO DATA" is indicated on the display section 9.

Then, whether the power switch 100 has been pushed or not is judged (step S15). When the power switch 100 has not been pushed, the process returns back to step 10 to continue the graphical display, and when the switch 100 has been pushed, the graphical display mode is finished and the power source of the body fat meter is turned off (step S16).

In case where the graph switch 106 is not pushed in Step 8, the process moves to a measurement mode.

In the measurement mode, the body fat meter is under the condition ready for measuring. The person to be measured selects one switch out of the personal switches 101 to 105 as a memory number having used for storing. Then the set switch 109 is pushed (step S17).

When the memory number is selected, the personal body information including the birth date, the sex and the height data, which is stored in a storage indicated by that number, is displayed on the display section 9 (step S18). This requests the person to be measured to confirm the correctness of the selected memory number. After a certain period of time, "0.0 kg" is automatically displayed on the display section 9.

Then the person to be measured put himself (herself) on the body fat meter main body 1. At that time, the person to be measured put himself (herself) thereon by bare feet so that his (her) toes and heels may come in contact with the electrodes 2A, 2B, 3A and 3B on the measuring surface of the body fat meter main body 1 respectively. When the body weight measuring device 6 in the body fat meter main body 1 senses the weight, the weight measurement is started (step S19).

Then the impedance is measured. At that time, the constant current generated by the high frequency constant current circuit 4 is applied through the electrodes 2A and 2B to respective toes so that the current is applied to between both feet including an abdomen or the lower half of his (her) body. At the same time, the voltage between the electrodes 3A and 3B is measured by the voltage measurement circuit 5 (step S20). Measured values of the body weight and the voltage are converted to the digital values by the A/D converter 7 and are sent to the CPU 12 in the control box 8.

The CPU 12 calculates the body fat rate and the body fat mass based on the received body weight value, voltage value and personal body information, and as a determined result, the body weight value and the body fat rate are numerically displayed on the display section 8 (step S21). The determined body weight value and body fat rate are stored in the storage device 14. At the same time, the date data from the timer device 15 is stored together therewith in the storage device 14 (step S22). Owing to this associative storing of the date data, the past body fat mass can be graphically displayed.

Further, the BMI is determined based on the determined body weight value and the stored height data to make a judgment of the body fat rate range, that is, whether it is proper, low or of obesity, and the result thereof is indicated on the display section 9 (step S23). When the body fat rate is within the range of 10 to 20% for man or 20 to 30% for woman, it is judged to be proper and when it is less or more than these value, it is judged to be low or of obesity respectively. These values are stored in the storage section 14 in advance and are used to make a comparison and a judgment by the CPU 12.

Then, the currently measured data is added further and the process moves to the graphical display mode of step S10 for the graphical display, where the transition of the body weight and the body fat mass can be observed as a graph display. Since the following operation is the same with that of the steps in the graphical display mode, it will be omitted.

Though one embodiment of the present invention has been described above taking the case of body fat meter in which the impedance is measured between feet, the present invention is not limited to this type of body fat meter but may be applied to other types of body fat meters in which the impedance is measured between both hands or between hand and foot or to still other type in which the body fat in various portion is measured by combining the measuring portions described above since the present invention is the invention relating to the display method of the body fat meter.

Though this embodiment shows an arrangement where the transition of the body fat mass is graphically displayed together with that of the body weight, the body fat mass may be replaced by the body fat rate or the body weight may not be displayed simultaneously in so far as the indexes relating to the body fat is graphically displayed in an easily sensible manner.

Though this embodiment shows a configuration where the control box is connected to the body fat meter main body by the code, other method may be employed using a wireless type data communication system by infrared or radio wave, and further, the control box may not be separated from but be incorporated into the body fat meter main body.

Though this embodiment shows a case where, as the indications of the body weight and the body fat mass, the daily, the weekly and the monthly variations or transitions thereof are displayed, the unit of measuring period may be changed properly in order to meet to a purpose of use.

Further, the display system of the present invention is not limited to the body fat meter for measuring the body fat, but may be applied to the display system of other devices for measuring or evaluating the bio-characteristic values or indexes such as total body water volume, muscle mass or fat free mass based on the measured bioelectric impedance value and the input personal body information.

As for the body weight scale, also the present invention may be applied thereto to display the variation of the body weight.

According to the bio-characteristic value measuring device of the present invention, since the short-term variation of the bio-characteristic values or indexes measured in the past days and the long-term variation thereof determined by averaging these values in each short-term period taking it as one unit of time period are displayed simultaneously, the transition thereof may be easily realized even if the daily measured values are likely to vary, which is preferable in the viewpoint of health care.

According to the body fat meter of the present invention, since the daily, the weekly and the monthly variations of the body fat are simultaneously displayed as the transition thereof, the user can observe the long-term transition of the body fat in an easily sensible manner. Further, in case where the variations of the body weight and the body fat mass are displayed simultaneously, a dangerous tendency to the living body that the body weight decreases but the body fat doesn't decrease may also be detected.

Accordingly, the body fat meter of the present invention allows the user to detect an unreasonable dieting where only the fat free tissue decreases but the body fat doesn't decrease, and provides the user with a safe and healthy weight and body fat management system.

What is claimed is:

1. A bio-characteristic value measuring device with graphical display comprising: a measuring device; a storage device; and a display device, whereby said measuring device measures a bio-characteristic value, said storage device stores a measured characteristic value, and said display device graphically displays variations of characteristic values in at least a first and a second units of time simultaneously, said characteristic values in said first unit of time being defined by stored characteristic values, and said characteristic values in said second unit of time being defined by average values of characteristic values calculated based on a plurality of characteristic values in said first unit of time.

2. A bio-characteristic value measuring device with graphical display comprising: a measuring device; an input device; an arithmetic device; a storage device; and a display device, whereby said measuring device is for measuring a bio-characteristic value, said input device is for inputting a personal body information of a person to be measured, said arithmetic device is for evaluating a bio-characteristic index of said person to be measured based on a measured bio-characteristic value and an input personal body information, said storage device is for storing an evaluated bio-characteristic index and said input personal body information, and said display device is for graphically displaying variations of characteristic values in at least a first and a second units of time simultaneously, said characteristic values in said first unit of time being defined by stored past bio-characteristic indexes, and said characteristic values in said second unit of time being defined by average values of characteristics values calculated based on a plurality of index values in said first unit of time.

3. A body weight scale comprising: a body weight measuring device; a storage device; and a display device, whereby said body weight measuring device measures a body weight, said storage device stores a measured body weight, and said display device simultaneously displays a plurality of variations among a daily variation, a weekly variation and a monthly variation of stored past body weight values.

4. A body fat meter comprising: an impedance measuring device; an input device; an arithmetic device; a storage device; and a display device, whereby said impedance measuring device is for measuring a bioelectrical impedance value, said input device is for inputting a personal body information of a person to be measured, said arithmetic device is for evaluating a body fat of said person to be measured based on a measured bioelectrical impedance value and an input personal body information, said storage device is for storing an evaluated body fat and said input personal body information, and said display device is for graphically displaying simultaneously a plurality of variations out of a daily, a weekly and a monthly variations of stored past body fat data.

5. A body fat meter comprising: an impedance measuring device; a weight measuring device; an input device; an arithmetic device; a storage device; and a display device, whereby said impedance measuring device is for measuring a bioelectrical impedance value, said weight measuring device is for measuring a body weight value, said input device is for inputting a personal body information of a person to be measured, said arithmetic device is for evaluating a body fat of said person to be measured based on a measured bioelectric impedance value and body weight value and an input personal body information, said storage device is for storing an evaluated body fat data, said measured body weight values and said input personal body information, and said display device is for graphically displaying simultaneously a plurality of variations out of a daily, a weekly and a monthly variations of stored past body fat data and stored past body weight values.

6. A body fat meter in accordance with claim 4 in which said display device graphically displays simultaneously all of said daily, said weekly and said monthly variations.

7. A body fat meter in accordance with claim 4 in which said body fat displayed on said display device is a body fat mass which means a weight thereof.

8. A body fat meter comprising: an impedance measuring device; an input device; an arithmetic device; a storage device; and a display device, wherein said impedance measuring device measures a bioelectrical impedance value, said input device is for inputting a personal body information of a person to be measured, said arithmetic device evaluates a body fat of said person to be measured based on a measured bioelectrical impedance value and an input personal body information, said storage device stores an evaluated body fat and said input personal body information, and said display device graphically displays simultaneously all of a daily variation of stored past body fat data over seven days, a weekly variation of stored past body fat data over twelve weeks and a monthly variation of stored past body fat data over twelve months.

9. A body fat meter comprising: an impedance measuring device; a weight measuring device; an input device; an arithmetic device; a storage device; and a display device, whereby said impedance measuring device measures a bioelectrical impedance value, said weight measuring device measures a body weight value, said input device is for inputting a personal body information of a person to be measured, said arithmetic device evaluates a body fat of said person to be measured based on a measured bioelectrical impedance value and a body weight value and an input personal body information, said storage device stores an evaluated body fat data and said input personal body information, and said display device graphically displays simultaneously all of a daily variation of stored past body fat data and stored past body weight values over seven days, a weekly variation of stored past body fat data and stored past body weight values over twelve weeks and a monthly variation of stored past body fat data and stored past body weight values over twelve months.

10. A body fat meter comprising: an impedance measuring device; an input device; an arithmetic device; a storage device; and a display device, wherein said impedance measuring device measures a bioelectrical impedance value, said input device is for inputting a personal body information of a person to be measured, said arithmetic device evaluates a body fat of said person to be measured based on a measured bioelectrical impedance value and an input personal body information, said storage device stores an evaluated body fat and said input personal body information, and said display device graphically displays simultaneously a plurality of variations out of a daily, a weekly and a monthly variations of stored past body fat data, and wherein said display device comprises a dot matrix type LCD, a bar graph is employed as a graph displayed on said dot matrix type LCD, and when a plurality of variations among said daily, said weekly and said monthly variations is displayed simultaneously, a variation in one period is indicated by all dots included in said bar graph showing values of said variations and another variation in another period adjacent to said one period is indicated only by dots for indicating said values of said another variation.

11. A body fat meter comprising: an impedance measuring device; a weight measuring device; an input device; an arithmetic device; a storage device; and a display device, wherein said impedance measuring device measures a bioelectrical impedance value, said weight measuring device measures a body weight value, said input device is for inputting a personal body information of a person to be measured, said arithmetic device evaluates a body fat of said person to be measured based on a measured bioelectrical impedance value and body weight value and an input personal body information, said storage device stores an evaluated body fat data, said measured body values and said input personal body information, and said display device graphically displays simultaneously a plurality of variations out of a daily, a weekly and a monthly variations of stored past body fat data and stored past body weight values, and wherein said display device comprises a dot matrix type LCD, a bar graph is employed as a graph displayed on said dot matrix type LCD, and when a plurality of variations among said daily, said weekly and said monthly variations is displayed simultaneously, a variation in one period is indicated by all dots included in said bar graph showing values of said variations and another variation in another period adjacent to said one period is indicated only by dots for indicating said values of said another variation.

* * * * *